United States Patent
Müller et al.

(10) Patent No.: US 7,235,697 B2
(45) Date of Patent: Jun. 26, 2007

(54) USE OF H2S-CONTAINING OFFGAS STREAMS FOR PREPARING SULFUR-CONTAINING PRODUCTS

(75) Inventors: Christian Müller, Mannheim (DE); Markus Weber, Ludwigshafen (DE); Eckhard Stroefer, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 11/302,614

(22) Filed: Dec. 14, 2005

(65) Prior Publication Data

US 2006/0128994 A1    Jun. 15, 2006

(30) Foreign Application Priority Data

Dec. 15, 2004   (DE)   ............. 10 2004 060 321

(51) Int. Cl.
*C07C 315/00* (2006.01)
*C07C 317/00* (2006.01)
*C07C 319/00* (2006.01)
*C07C 321/00* (2006.01)
*C07C 381/00* (2006.01)

(52) U.S. Cl. .................. 568/18; 568/21; 568/38; 568/61

(58) Field of Classification Search ........... 568/18, 568/21, 38, 61
See application file for complete search history.

(56) References Cited

U.S. PATENT DOCUMENTS

| | | | |
|---|---|---|---|
| 3,214,386 A | | 10/1965 | Warner et al. |
| 3,419,614 A | * | 12/1968 | Doss ................. 564/500 |
| 3,459,089 A | * | 8/1969 | Clark ................. 83/658 |
| 3,459,809 A | * | 8/1969 | Ishida et al. ............ 568/72 |
| 4,093,701 A | | 6/1978 | Butwell |
| 4,153,674 A | | 5/1979 | Verloop et al. |
| 4,638,093 A | * | 1/1987 | Fried ................. 568/73 |
| 5,453,544 A | * | 9/1995 | Giacobbe ............ 568/72 |

FOREIGN PATENT DOCUMENTS

| | | |
|---|---|---|
| DE | 27 54 118 | 6/1978 |
| EP | 0 122 654 | 10/1984 |
| GB | 625646 | 7/1949 |

OTHER PUBLICATIONS

P. Bapseres, "La synthése des mercaptans", *Chimie & Industrie*, vol. 90, No. 4, pp. 358-369 (Oct. 1963).[Lines 5-11].
J. F. Frantz et al., "A new process for dodecyl mercaptan", *Chem. Eng. Prog.*, vol. 59, pp. 68-79 (1963).
A. F. Holleman et al., "Lehrbuch der Anorganischen Chemie", (*Textbook of Inorganic Chemistry*), de Gruyter, p. 486 (1985), *[at p. 3, Lines 26-31]*.
*Ullman's Encyclopedia of Industrial Chemistry*, 6th edition, 2000, Electronic Release (Wiley VCH Verlag GmbH, Weinheim, Deutschland, 2000) Chapter 1.3.2.

\* cited by examiner

*Primary Examiner*—Thurman K. Page
*Assistant Examiner*—Chukwuma Nwaonicha
(74) *Attorney, Agent, or Firm*—Connolly Bove Lodge & Hutz LLP

(57) ABSTRACT

The present invention relates to a process for preparing sulfur-containing compounds of the general formula I

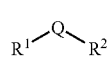

in which Q, $R^1$ and $R^2$ are each independently defined as follows:
Q: —S— or —S—S—,
$R^1$: hydrogen or saturated or unsaturated, linear or branched $C_1$-$C_{30}$-alkyl radical,
$R^2$: hydrogen or saturated or unsaturated, linear or branched $C_1$-$C_{30}$-alkyl radical,
where $R^1$ and $R^2$ are not simultaneously hydrogen, by reacting a mixed gas stream comprising hydrogen sulfide, with or without oxygen, with linear or branched $C_1$-$C_{30}$-olefins, which comprises carrying out the reaction in the presence of water and carbon dioxide at a pressure of from 2 to 325 bar.

7 Claims, No Drawings

USE OF H2S-CONTAINING OFFGAS STREAMS FOR PREPARING SULFUR-CONTAINING PRODUCTS

The present invention relates to a process for preparing thiols, thioethers and disulfides by reacting olefins with hydrogen sulfide in the presence of water and carbon dioxide, with or without oxygen.

Alkyl thiols having from 10 to 30 carbon atoms are known compounds. Alkyl thiols or mixtures of these compounds are typically obtained by acid-catalyzed electrophilic addition of hydrogen sulfide ($H_2S$) to olefins. According to the Markovnikov rule, this forms a tertiary thiol from olefins which have at least three alkyl substituents on their double bond and a secondary thiol from linear olefins.

Secondary thiols find use as fragrances, as components in lubricant formulations and as hardeners for epoxy resins. In addition, they are used advantageously as intermediates in the preparation of surface-active compounds.

Tertiary thiols are used as molar mass regulators in polymerizations, especially for free-radical polymerizations of vinylic monomers, for example polymerization of butadiene, styrene, carboxylated styrene, acrylic acid, acrylonitrile, acrylic esters, vinyl ethers or mixtures thereof.

Ullmann's Encyclopedia of Industrial Chemistry, 6th edition, 2000 Electronic Release (Wiley VCH Verlag GmbH, Weinheim, Germany, 2000) gives an overview of known methods for preparing alkyl thiols under the heading "Thiols and Organic Sulfides", point 1.3., "Production of Aliphatic Thiols", under point 1.3.2. "From Alkenes". Common olefin mixtures which are reacted with hydrogen sulfide over an acidic catalyst to give tert-dodecyl thiol are trimerized isobutene and tetramerized propene. Both are known mixtures of highly branched alkenes which were formerly used to a relatively great extent for the preparation of an ionic surfactants. In the selection of the catalyst, it has to be ensured that the olefin or olefin mixture used does not have too high a polymerization tendency over the selected catalyst, since the catalyst is deactivated if oligomers or polymers accumulate on it, which necessitate a more frequent change of catalyst and can thus impair the economic viability of the process.

P. Bapseres, Chim. Ind. (Paris) 90 (1963), p. 358 ff. discloses a process for preparing tert-dodecyl thiol from tetrameric propene and hydrogen sulfide at –40° C. in the presence of a boron trifluoride or aluminum trichloride catalyst. J. F. Franz and K. I. Glass, Chem. Eng. Prog. 59 (volume 7), 1963, page 68 ff. teach a process for preparing tert-dodecyl thiol from tetrameric propene and hydrogen sulfide at from 49 to 71° C. in the presence of a boron trifluoride catalyst.

EP 0122654 discloses a process for preparing secondary thiols having from 10 to 22 carbon atoms at a temperature of from 40 to 140° C. and a pressure of from 10 to 100 bar, likewise in the presence of a zeolite as catalyst.

GB 625 646 describes a process for hydrogen sulfide addition to trimeric isobutene with a clay catalyst which is activated either with sulfuric or phosphoric acid.

U.S. Pat. No. 3,214,386 teaches the use of a mixture of phosphoric acid, boron trifluoride and an alcohol having from 1 to 5 carbon atoms as a catalyst in the addition of hydrogen sulfide to double bonds of olefins.

In the prior art processes for reacting hydrogen sulfide with olefins, solid acids such as ion exchange resins (IOT) and zeolites are used as catalysts. In general, it is necessary in the prior art processes to purify the hydrogen sulfide by chemical and/or physical methods before the reaction.

Disadvantages of the use of solid compounds as a catalyst are:

Transport processes within the solid (pores) often constitute the rate-limiting reaction step. Large reactors with large amounts of catalyst are the consequence.

Ion exchange resins are thermally sensitive and, owing to the exothermic reaction, require constant heat removal from reactive sites. This has the consequence of expensive parallel design, for example in the form of tube bundle reactors.

Ion exchange resins are mechanically sensitive and can be used without significant attrition only in fixed beds.

Zeolites lose their acidic action very rapidly and have to be regenerated in a costly and inconvenient manner Outside the reactor, for example at 500° C.

Zeolite powders consist partly of very small particles in the range of a few micrometers which have to be removed from the reaction mixture in a very costly and inconvenient manner. When the removal takes place outside the reactor, it is also necessary to return the catalyst.

Fixed beds composed of moldings based on zeolite powder are mechanically comminuted during the flow-through with, for example, liquids (for the disadvantage of small particles see above).

In the known processes for reacting olefins with hydrogen sulfide, the secondary components which are present in a mixture with hydrogen sulfide, such as water and/or carbon dioxide, are generally removed before the reaction by customary preceding physical and/or chemical processes.

In industry, hydrogen sulfide is obtained in huge amounts in crude oil desulfurization and in the production of certain "acidic" natural gases; in addition, hydrogen sulfide can be obtained from heating gas, coking oven gas and other gases produced from coal (water gas, synthesis gas) (from Hollemann Wiberg, Lehrbuch der Anorganischen Chemie [Textbook of Inorganic Chemistry], deGruyter 1985, page 486).

Suitable methods for removing hydrogen sulfide from mixed gas streams are, for example, adsorption in an ethanolamine solution (Girbotol process) or chemical conversion (Claus process). The Claus process is an important process for obtaining sulfur by oxidation of hydrogen sulfide by $SO_2$. A portion of the sulfur obtained in this way is subsequently used in the synthesis of hydrogen sulfide.

U.S. Pat. No. 4,093,701 discloses a process for selectively removing hydrogen sulfide from an offgas mixture which comprises carbon dioxide in addition to hydrogen sulfide, by reaction with an aqueous alkanolamine solution.

DE 27 54 118 discloses a process for removing hydrogen sulfide from offgases by reacting offgas streams comprising hydrogen sulfide and carbon dioxide with hydrogen over a catalyst at from 180 to 450° C.

It is an object of the present invention to provide a process for preparing thiols, thioethers and disulfides by reacting olefins with hydrogen sulfide, with or without oxygen, in which mixed gas streams which comprise hydrogen sulfide may be used without hydrogen sulfide having to be removed by physical and/or chemical processes and/or purified before the reaction.

This object is achieved by a process for preparing sulfur-containing compounds of the general formula (I)

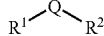

in which Q, $R^1$ and $R^2$ are each independently defined as follows:
Q: —S— or —S—S—,
$R^1$: hydrogen or saturated or unsaturated, linear or branched $C_1$-$C_{30}$-alkyl radical,
$R^2$: hydrogen or saturated or unsaturated, linear or branched $C_1$-$C_{30}$-alkyl radical,
where $R^1$ and $R^2$ are not simultaneously hydrogen, by reacting a mixed gas stream comprising hydrogen sulfide, with or without oxygen, with linear or branched $C_1$-$C_{30}$-olefins, wherein the reaction is carried out in the presence of water and carbon dioxide at a pressure of from 2 to 325 bar.

The process according to the invention is carried out in the presence of carbon dioxide and water. In a preferred embodiment, water and carbon dioxide are already present in the mixed gas stream, i.e. water and carbon dioxide are consequently not additionally added to the reaction mixture.

The process according to the invention affords sulfur-containing compounds of the general formula I

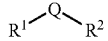

In which Q, $R^1$ and $R^2$ are each independently defined as follows:
Q: —S— or —S—S—,
$R^1$: hydrogen or saturated or unsaturated, linear or branched $C_1$-$C_{30}$-alkyl radical, preferably $C_8$-$C_{22}$-alkyl radical, more preferably $C_{10}$-$C_{22}$-alkyl radical, most preferably $C_{10}$-$C_{16}$-alkyl radical,
$R^2$: hydrogen or saturated or unsaturated, linear or branched $C_1$-$C_{30}$-alkyl radical, preferably $C_8$-$C_{22}$-alkyl radical, more preferably $C_{10}$-$C_{22}$-alkyl radical, most preferably $C_{10}$-$C_{16}$-alkyl radical,
where $R^1$ and $R^2$ are not simultaneously hydrogen.

The $R^1$ and $R^2$ radicals may additionally be substituted. Suitable substituents are, for example, saturated, unsaturated and/or aromatic radicals having from 1 to 20 carbon atoms or functional groups such as halogens, hydroxyl, aldehyde, keto, carboxyl, amide, imide or ester groups. The carbon substituents having from 1 to 20 carbon atoms may also be substituted with, for example, the functional groups mentioned.

Q has the definition of —S— or —S—S—. When no oxygen is present in addition to hydrogen sulfide, carbon dioxide and water in the mixed gas which can be used in accordance with the invention, Q is —S—, which means that thiols or thioethers are formed. When oxygen is present in addition to hydrogen sulfide, carbon dioxide and water in the inventive mixed gas, Q has the definition of —S—S—, i.e. disulfides are formed in the process according to the invention. In the presence of oxygen in the mixed gas which can be used in accordance with the invention, compounds in which Q is —S— may also be present in addition to compounds in which Q is —S—S—.

In a very particularly preferred embodiment, $R^1$ and $R^2$ in the general formula (I) are each independently hydrogen or a saturated alkyl radical having 12 carbon atoms, where $R^1$ and $R^2$ are not simultaneously hydrogen.

In the process of the present invention, $C_1$-$C_{30}$-olefins, preferably $C_8$-$C_{22}$-olefins, more preferably $C_{10}$-$C_{22}$-olefins, even more preferably $C_{10}$-$C_{16}$-olefins, especially preferably $C_{12}$-olefins, are used. It is possible to use mixtures of olefins having different carbon number and/or different substitution pattern, or uniform olefins. These olefins or mixtures of olefins may be obtained, for example, by cracking of paraffin wax or oligomerization of ethene. The resulting oligomerization products have for the most part a linear structure, while olefins which are obtained by oligomerization of propene and/or butenes are branched.

The olefins which can be used in the process according to the invention may have one or more double bond(s) per molecule. Preference is given to using olefins which have one double bond per molecule, known as monoolefins.

The olefins which can be used in accordance with the invention may either be α-olefins having a terminal double bond or a double bond may also be present internally in the hydrocarbon.

Such linear internal olefins may be obtained, for example, by chlorination—dechlorination of paraffins, by paraffin dehydrogenation and by α-olefin isomerization. As a result of the preparation process, the olefins or olefin mixtures which can be used may comprise impurities, for example aromatic compounds and/or saturated hydrocarbons, in a proportion of up to 3% by weight. These impurities do not influence the process according to the invention.

The olefins may be linear or have one or more alkyl substituents along the main carbon chain. When olefins whose double bond is terminal or has two substituents are used in the process according to the invention, secondary sulfur compounds are obtained, i.e. the carbon atom bearing the —S—, —S—S—, —SH or —S—S—H functionality is bonded to two further carbon atoms. When olefins are used which bear at least three substituents on the double bond, tertiary sulfur compounds are obtained, i.e. the carbon atom bearing the —S—, —S—S—, —SH or —S—S—H functionality is bonded to three further carbon atoms. Preference is given to preparing tertiary alkyl thiols by the process according to the invention.

Very particular preference is given to using olefins having 12 carbon atoms in the process according to the invention. As a result of the preparation process, the olefin component used may have contaminations by olefins having a carbon number deviating from 12 up to a proportion of 5% by weight, preferably of 3% by weight.

The dodecenes which can be used in the process according to the invention correspond especially preferably to one or more olefins which are derived from the following compounds:

olefins which are derived from n-dodecane (I)

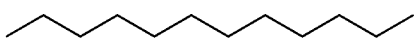

olefins which are derived from 5-methyl-n-undecane (II)

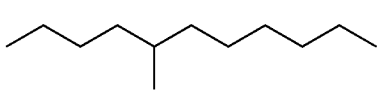

olefins which are derived from 4-ethyl-n-decane (III)

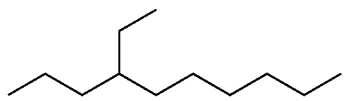

III olefins which are derived from 5,6-dimethyl-n-decane (IV)

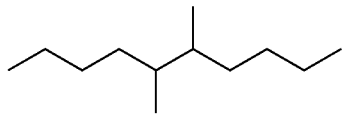

IV olefins which are derived from 5-ethyl-6-methyl-n-nonane (V)

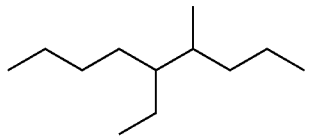

V and olefins which are derived from 4,5-diethyl-n-octane (VI)

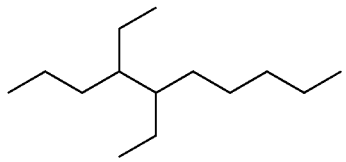

VI

"Derived olefin" refers to an olefin which is formed in a formal sense from the alkane in question by dehydrogenation, i.e. removal of two hydrogen atoms from adjacent carbon atoms to form a double bond between these carbon atoms, although the carbon skeleton remains unchanged. It is neither possible nor necessary to precisely specify the position of the double bond, since the double bond migrates along the carbon chain both in the course of customary methods of preparing such mixtures (for example as specified below) and in the course of the reaction of olefins with hydrogen sulfide. The addition of hydrogen sulfide to olefins in the presence of acidic catalysts is a reversible reaction, although the double bond can be formed differently to the way in which it was present beforehand in the carbon chain. Overall, the position of the double bond in the carbon skeletons and thus also the position of the thiol group are established with thermodynamic or else kinetic control under the conditions employed.

In the process according to the invention, preference is given to using a hydrocarbon mixture which comprises at least 10% by weight, preferably at least 12% by weight and more preferably at least 13% by weight, and at most 18% by weight, preferably at most 16% by weight and more preferably at most 15% by weight, of olefin derived from n-dodecane (I), at least 25% by weight, preferably at least 30% by weight and more preferably at least 34% by weight, and at most 40% by weight, preferably at most 38% by weight and more preferably at most 36% by weight, of olefin derived from 5-methyl-n-undecane (II), at least 25% by weight, preferably at least 30% by weight and more preferably at least 32% by weight, and at most 40% by weight, preferably at most 38% by weight and more preferably at most 34% by weight, of olefin derived from 4-ethyl-n-decane (III), at least 2% by weight, preferably at least 4% by weight and more preferably at least 5% by weight, and at most 8% by weight, preferably at most 7% by weight, of olefin derived from 5,6-dimethyl-n-decane (IV), at least 5% by weight, preferably at least 6% by weight and more preferably at least 8% by weight, and at most 12% by weight, preferably at most 10% by weight, of olefin derived from 5-ethyl-6-methyl-n-nonane (V), at least 1% by weight, preferably at least 2% by weight, and at most 5% by weight, preferably at most 4% by weight and more preferably at most 3.5% by weight, of olefin derived from 4,5-diethyl-n-octane (VI), and at most 5% by weight, preferably at most 3% by weight, of other hydrocarbons, with the proviso that the sum of the proportions of the components is 100% by weight.

Very particular preference is given to preparing tert-dodecyl thiol from dodecene and hydrogen sulfide by the process according to the invention. It is also possible for primary and/or secondary dodecyl thiols to be present in addition to tertiary dodecyl thiols.

The configuration (cis or trans configuration isomerism) of the olefins used is unimportant. In general, the olefins are used in the configuration (or in the form of the mixture of configurational isomers) in which they are generated, which usually corresponds to the thermodynamically predefined relative stability of the isomers.

The reaction of olefins (VIII) with hydrogen sulfide to give thiols (IX) proceeds generally by the following reaction scheme

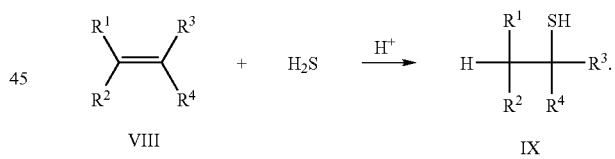

The thiol (IX) formed during the reaction may react with a further equivalent of olefin (VIII) to give the corresponding thioether (X)

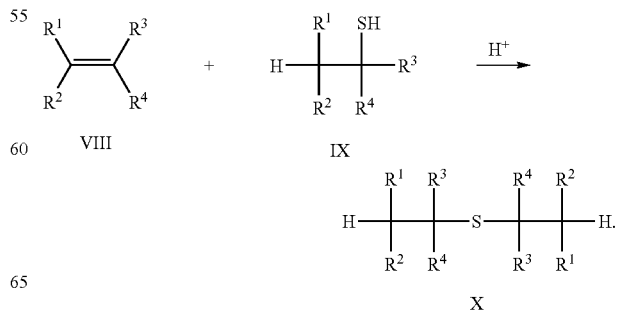

When the mixed gas stream which can be used in accordance with the invention also comprises oxygen in addition to hydrogen sulfide, carbon dioxide and water, the thiol (IX) formed reacts by the following scheme with a half molecule of oxygen and one molecule of hydrogen sulfide to give disulfide (XI)

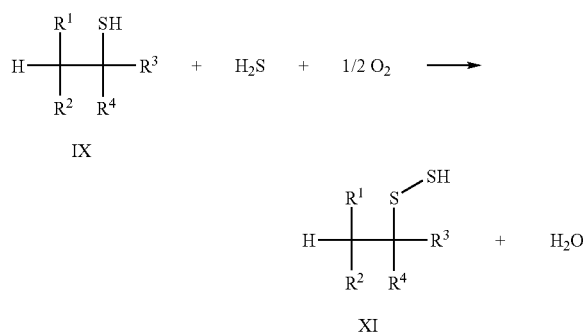

or two molecules of thiol (IX) react with a half molecule of oxygen to give disulfide

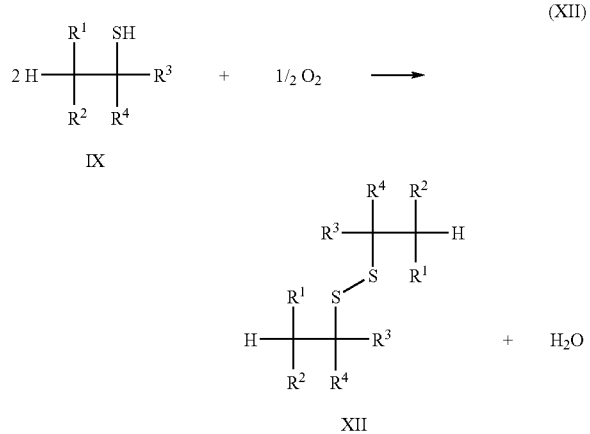

The process according to the invention is notable in that, depending on the composition of the mixed gas used, the abovementioned sulfur-containing compounds, thiols, thioethers and/or disulfides, may be obtained with one or two alkyl substituents. The corresponding disulfides are formed when the mixed gas used also comprises oxygen in addition to hydrogen sulfide, carbon dioxide and water. In the presence of oxygen, the process according to the invention is a process for preparing disulfides in one reactor without isolation and/or purification of intermediates.

The process according to the invention may be carried out continuously, semi-continuously or batchwise. In one embodiment, the process according to the invention may be operated continuously, i.e. the product is removed continuously and the substrates are fed continuously according to their consumption, so that constant concentrations of all substances present are present on average in the reaction vessel. Reaction vessels suitable for the continuous procedure are known to those skilled in the art. Examples are tubular reactors, stirred reactors, circulation reactors.

In a further embodiment, the process according to the invention may be carried out semicontinuously, i.e. the substrates are mixed, the reaction is started and products formed are removed continuously, for example by distillation.

In the batchwise procedure, the substrates involved are mixed, the reaction is started and, on completion of the reaction, the reaction mixture as a whole is worked up by suitable methods, for example distillation.

At the start of the reaction, carbon dioxide and water which are present in the mixed gas which can be used in accordance with the invention form carbonic acid $H_2O$ (l)+$CO_2$(eq.)→$H_2CO_3$(eq.).

It has been found that the carbonic acid $H_2CO_3$ formed from carbon dioxide and water under pressure in the mixed gas, if appropriate with addition of further water, is suitable as a catalyst for preparing thiols, sulfides or disulfides from the olefins and hydrogen sulfide present in the mixed gas.

An advantageous feature of the process of the present invention is that the catalytically active species is formed from compounds which are already present in the substrate to be used, the mixed gas. Consequently, it is not necessary to introduce any further catalysts, liquid or solid, into the inventive reaction mixture. This results in a greatly simplified reaction and the avoidance of the mentioned disadvantages which occur when solid acidic catalysts are used.

In a preferred embodiment, the inventive reaction is carried out at a pressure of from 10 to 100 bar, more preferably from 15 to 50 bar.

In a preferred embodiment, the process according to the invention is carried out at a temperature of from 0 to 100° C., more preferably from 5 to 80° C., most preferably from 30 to 60° C.

Depending on the water content of the feedstocks, additional water is added to the reaction mixture if appropriate. In a preferred embodiment, water is present in the reaction mixture to an extent of from 0.1 to 50% by weight, more preferably to an extent of from 10 to 40% by weight, most preferably to an extent of from 20 to 30% by weight.

After a conversion of generally >85%, preferably >90%, more preferably >95%, has been achieved in the process according to the invention, the reaction mixture is decompressed, i.e. the pressure in the reaction vessel is lowered to standard pressure, as a result of which unreacted gas fractions are desorbed. If appropriate, the reaction mixture may be heated to up to 100° C. to release the gas fractions which are still present.

The sulfur-containing compounds prepared by the process according to the invention may, if appropriate, on completion of the reaction, be worked up and/or purified by all methods known to those skilled in the art. Examples include phase separation, extraction, distillation.

The process according to the invention may be carried out in the presence or in the absence of a further solvent in addition to water. Preference is given to carrying out the process in the presence of water and the absence of further solvents.

When the mixed gas used in the process according to the invention also comprises oxygen in addition to hydrogen sulfide, carbon dioxide and water, disulfides of the formula (XI) and/or (XII) are formed. The oxygen present in the mixed gas stream may stem from the reaction from which the mixed gas stream originates. It is also possible in accordance with the invention that oxygen is added to the mixed gas stream before it is introduced into the reaction vessel. In this case, the oxygen or an oxygen-containing gas is added to such an extent that it is present in the correct amount for the desired chemical reaction. Amounts of oxygen suitable for the process according to the invention are, for example, from 0.1 to 10% by weight, preferably from 2 to 6% by weight, more preferably from 3 to 4% by weight.

In a preferred embodiment, the mixed gas which can be used in the process according to the invention stems from the offgas stream of a chemical process. This offgas stream may stem from all chemical reactions in which carbon dioxide, with or without oxygen, are also present in addition to hydrogen sulfide in the offgas stream. Examples of suitable chemical processes are processes for producing synthesis gas or processes in which heating gas, coking oven gas or other gases produced from coal are formed.

The offgas which leaves the reaction vessel after the reaction, owing to the consumption of hydrogen sulfide to prepare the sulfur-containing compounds, has a lower proportion of hydrogen sulfide than the mixed gas which has been used as the substrate in the reaction. Depending on the stoichiometric ratio $n(H_2S)/n$(double bonds) of hydrogen sulfide to olefins in the reaction mixture, this offgas may be freed fully of hydrogen sulfide.

In the context of the present application, hydrogen sulfide-free means a content of hydrogen sulfide in the offgas of the process according to the invention of $\leq 0.5\%$, preferably $\leq 0.1\%$, more preferably $\leq 0.0001\%$, most preferably $\leq 0.00002\%$.

The process of the present invention is thus also suitable for cleaning hydrogen sulfide-containing mixed gas streams in order to obtain hydrogen sulfide-free off-gases.

Advantages of the process according to the invention are:

In the preparation of sulfur-containing compounds, the hydrogen sulfide used does not have to be purified beforehand in a costly inconvenient manner with physical and/or chemical processes.

As a result of the use of the carbon dioxide present in the mixed gas stream used as the catalytically active component in the process according to the invention, it is not necessary to add any further catalyst, as a result of which the disadvantages already mentioned above, for instance when using a solid acidic catalyst, can be obviated.

The process according to the invention may be used to clean hydrogen sulfide-containing mixed gas streams which are obtained on a large scale in chemical processes.

EXAMPLES

Example 1

12 g of water and 40 g of dodecene are introduced into the plant through a funnel. After the plant has been sealed, the reaction mixing pump is put into operation (rotation rate: 2800 min$^{-1}$) and the entire pumped circulation system, which is manufactured in jacketed design including the pump head, is brought to the start temperature of 30° C. The reaction is started by stepwise injection of first 10 bar of carbon dioxide and then 20 bar of hydrogen sulfide gas to a total pressure of approx. 31 bar. During the experiment, the $H_2S$ feed of the reactor system remains open, so that the amount of hydrogen sulfide which has reacted can be replenished into the reaction system. During the next 2 hours, the mixture is heated uniformly to 60° C. After 3 further hours, by means of pressure reduction at the withdrawal valve and additional heating to 100° C., all dissolved gas constituents are removed from the biphasic liquid sample. The composition of the organic liquid phase (upper phase) is analyzed by means of gas chromatography, and a distinction can be drawn between reactant (olefin), main product (thiol) and secondary component (thioether).

TABLE 1

| | GC analysis result [percent by mass] | | |
|---|---|---|---|
| | Dodecene | Thiol | Thioether |
| $CO_2$/water Carbonic acid | 3.5 | 93.5 | 3.0 |

Example 2

The following reaction is carried out in a stirred autoclave (V=0.3 l) which is equipped with a sparging stirrer, baffles and a heatable jacket. Dodecene and water are introduced before the reactor is sealed. Subsequently, the reactor contents are heated to the desired reaction temperature with the stirrer motor running at high speed, and the air-containing gas phase of the reactor is displaced by repeatedly injecting 10 bar of carbon dioxide, and the pressure of the last flushing operation on the system is allowed to stand. With the stirrer motor at rest, hydrogen sulfide is injected into the system to the desired reaction pressure and the stirrer of the autoclave is started immediately thereafter. During the experiment, the $H_2S$ feed of the reactor is open, so that the amount of hydrogen sulfide which has reacted is replenished into the reaction system. During the next two hours, the mixture is heated uniformly to 60° C. After 3 further hours, by means of pressure reduction at the withdrawal valve and additional heating to 100° C., all dissolved gas constituents are removed from the biphasic liquid sample. These experiments are evaluated quantitatively and qualitatively by the $H_2S$ consumption against time and gas chromatography analyses of the liquid phase. The table 2 which follows compares two experiments which are carried out virtually identically apart from the water addition. Without water addition, only the amount of water entrained by the olefin is present in the system (approx. 50 ppm) and there is hardly any noticeable reaction of the olefinic double bond.

TABLE 2

| Acid | Water [g] | Dodecene [g] | Temp. [° C.] | $CO_2$ pressure [bar] | $H_2S$ pressure [bar] | Rotation rate [min$^{-1}$] | Time [min] | GC analysis result [percent by mass] | | |
|---|---|---|---|---|---|---|---|---|---|---|
| | | | | | | | | Dodecene | Thiol | Thioether |
| $CO_2$ | 0 | 60 | 30–60 | 10 | 15 | 1600 | 300 | 99.7 | 0.2 | 0.1 |
| $CO_2$/water Carbonic acid | 20 | 60 | 30–60 | 10 | 15 | 1600 | 300 | 3.9 | 93.1 | 3.0 |

What is claimed is:

1. A process for preparing sulfur-containing compounds of the general formula I

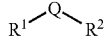   I in which Q, $R^1$ and $R^2$ are each independently defined as follows:
Q: —S—,
$R^1$: hydrogen or saturated or unsaturated, linear or branched $C_1$-$C_{30}$-alkyl radical,
$R^2$: hydrogen or saturated or unsaturated, linear or branched $C_1$-$C_{30}$-alkyl radical,
where $R^1$ and $R^2$ are not simultaneously hydrogen, by reacting a mixed gas stream comprising hydrogen sulfide, with or without oxygen, with linear or branched $C_1$-$C_{30}$-olefins, which comprises carrying out the reaction in the presence of water and carbon dioxide at a pressure of from 2 to 325 bar.

2. The process according to claim 1, wherein water is present in the reaction mixture to an extent of from 0.1 to 50% by weight.

3. The process according to claim 1, which is carried out at a pressure of from 10 to 100 bar.

4. The process according to claim 1, wherein $R^1$ and $R^2$ are each independently hydrogen or saturated or unsaturated, linear or branched $C_8$-$C_{22}$-alkyl radical, where $R^1$ and $R^2$ are not simultaneously hydrogen.

5. The process according to claim 1, wherein $R^1$ and $R^2$ are each independently hydrogen or a saturated alkyl radical having 12 carbon atoms, where $R^1$ and $R^2$ are not simultaneously hydrogen.

6. The process according to claim 1, wherein tert-dodecyl thiol is prepared from dodecene.

7. The process according to claim 1, wherein the mixed gas stems from the offgas stream of a chemical process.

* * * * *